United States Patent [19]

Cummins

[11] 4,141,833
[45] Feb. 27, 1979

[54] ANCHORING MEANS FOR TLC SYRINGE AND APPARATUS

[75] Inventor: Judith G. Cummins, Libertyville, Ill.

[73] Assignee: Analytical Instrument Specialties, Inc., Libertyville, Ill.

[21] Appl. No.: 789,648

[22] Filed: Apr. 21, 1977

[51] Int. Cl.² .............................................. B01D 15/08
[52] U.S. Cl. ................................................. 210/198 C
[58] Field of Search .................. 210/198 C, DIG. 24; 417/437; 128/124, 231; 222/206–210, 386; 73/422 GC

[56] References Cited

U.S. PATENT DOCUMENTS

| | | | |
|---|---|---|---|
| 3,035,616 | 5/1962 | Hamilton | 222/386 X |
| 3,366,286 | 1/1968 | Kloehn | 222/386 |
| 3,417,904 | 12/1968 | McLaw | 222/386 |
| 3,738,493 | 6/1973 | Cummins et al. | 210/198 C |

Primary Examiner—John Adee

Attorney, Agent, or Firm—Knechtel, Valentino, Demeur & Dallas

[57] ABSTRACT

A sample discharge syringe especially designed to be used with thin layer chromatography apparatus or TLC. The new syringe is designed to be used as one of a gang of syringes aligned on apparatus as disclosed and claimed in U.S. Pat. No. 3,738,493. The syringe has an anchoring button securely mounted at an area at the forward end of the syringe barrel or on the rear part of the needle which is mounted to the syringe barrel in communication with its interior passageway. The anchoring button has a flange plate in which the radial axis is normal to the elongated axis of the needle and the syringe body. This anchoring plate engages an anchoring rack on the top surface of the TLC apparatus which has a transverse slot to accommodate the flange plate and a slot normal to the transverse slot to accommodate the needle. A two-point hold down system is thus provided with the new syringe to assure immobilization of the gang of syringes as TLC samples are discharged when the needle tips are lowered to the TLC plate.

7 Claims, 6 Drawing Figures

ANCHORING MEANS FOR TLC SYRINGE AND APPARATUS

FIELD OF THE INVENTION

This invention relates to a new syringe for discharging TLC samples; and particularly, the invention relates to such a syringe with improved means for securing the syringe against movement, particularly forward and backward movement.

BACKGROUND OF THE INVENTION

A TLC apparatus has been disclosed and claimed in U.S. Pat. No. 3,738,493. Briefly, a power unit and controls are provided to advance a pusher bar at a constant rate of speed against the plungers of a gang of syringes to commonly discharge TLC samples at a constant rate on a TLC plate. Means are provided to gently place the tips of the needles on a TLC plate so that the sample may be deposited on the plate with little concern for losses through evaporation.

The gang of syringes are aligned in a rack held by a releaseable hold down bar to immobilize the gang of syringes.

OBJECTS AND ADVANTAGES OF THE INVENTION

One important object of the present invention is to provide a new TLC sample discharge syringe which can even more reliably be secured against displacement when placed on the top of a TLC apparatus. In particular, it is an object to provide such a syringe which can be held on a TLC apparatus in secured relationship against forward and backward sliding displacement to prevent the lowered needles from scoring the TLC plate surface.

Another important object is to provide improved cooperating anchoring means on a TLC syringe to prevent undesired movement which does away with former requirements of increasing potentially damaging hold down pressures on the syringe body.

Another important object of the present invention is to provide an anchoring rack fixed to the surface of the TLC apparatus so that said new syringe with the improved anchoring means can simply, quickly and reliably be engaged and disengaged to said anchoring rack. Each of the plurality of syringes is thus secured against displacement in the two directions possible: axial displacement or forward and backward movement of the syringe barrel; and lateral displacement along a radial axis which is normal to the long axis of the syringe barrel.

DESCRIPTION OF THE VIEWS OF THE INVENTION

The foregoing objects and advantages are attained, together with still other objects of the invention which will occur to practitioners from considering the invention of the following disclosure which includes drawings wherein:

FIG. 1 is a perspective view, somewhat schematic, illustrating the type of TLC apparatus disclosed and claimed in U.S. Pat. No. 3,738,493, with modifications to allow combined use with the new syringes in an advantageous manner.

SUMMARY OF THE INVENTION

A TLC syringe, with improved anchoring features, provides an anchoring button fixed securely to a mounting area which may be the forward end of the syringe body, or the rear of the needle which is mounted to the forward end of the syringe body in communication with the passageway of the syringe body.

The anchoring button is a unitary element which has a cylindrical stub defining a passageway that closely corresponds to the selective mounting area, that is, the rearward end of the needle or the forward end of the syringe body. The cylindrical stub is variously mounted in secured manner to the selective mounting area. For example, in the preferred form, the anchoring element is a deformable metal so the cylindrical stub may be crimped and interlocked to the metal needle. As another example, a cylindrical stub on the anchoring element will be of increased diameter to closely engage the forward end of the syringe body. Such a form of the cylindrical stub may be formed of other materials, such as plastic, and may be bonded to the end of the syringe body.

Integrally mounted to the forward or discharge end of the cylindrical stub is a flange element or plate. Such flange plate, of course, does not obscure or reduce the passageway of the cylindrical stub in any way.

The anchoring element or button fixed to the selective area of the syringe engages an anchoring rack fixed to the top surface of the TLC apparatus. In particular, the anchoring button of each syringe engages one aligned seat of a plurality of seats distributed along the length of the elongated rack. Each anchoring seat includes a transverse slot to seat the flange of the anchoring element, and a slot or groove normal to the transverse slot. The normal groove seats the needle. In the preferred form, the transverse slot is formed by incline walls to facilitate entry and removal of the flange plate. The needle groove is also lowered relative to said transverse slot.

DETAILED DESCRIPTION OF THE INVENTION

Figure 1:
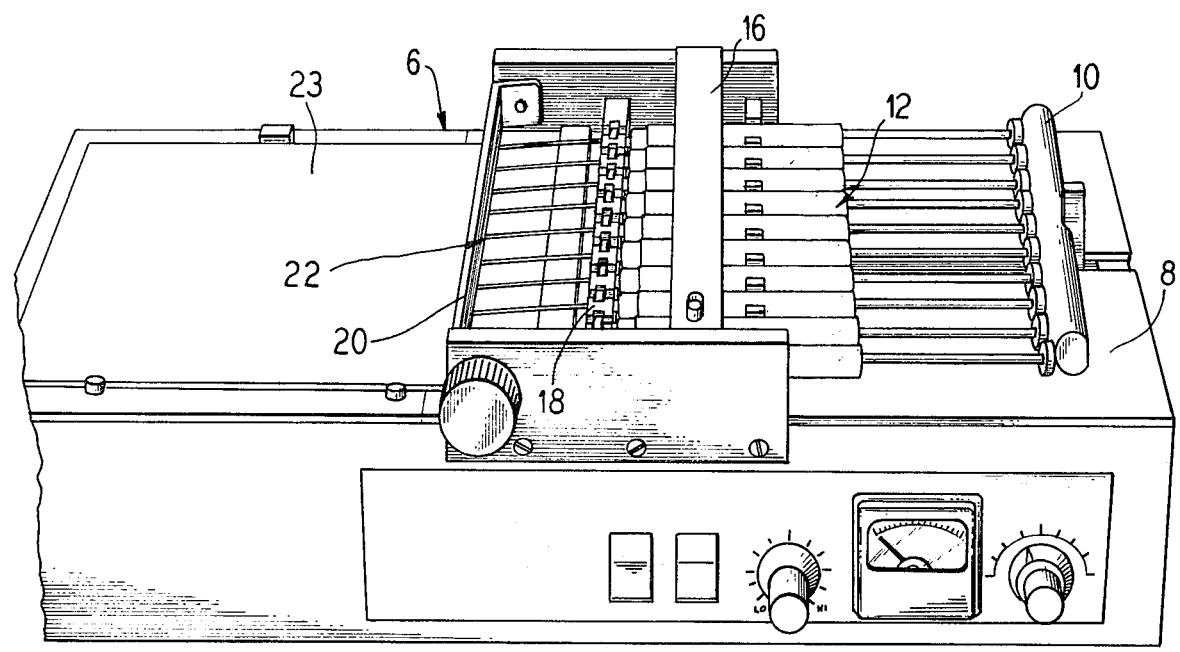

Considering first the TLC apparatus shown in FIG. 1, certain parts will be described which are necessary to an understanding of the invention. Other elements and parts will not be described, but can be determined from examination of U.S. Pat. No. 3,738,493. The TLC apparatus is shown generally as 6 and the top surface indicated at 8. The features of such a type of apparatus is the provision of a common pusher bar 10 which is advanced at a constant, but variable speed, to discharge TLC samples from a gang of syringes indicated collectively at 12. The body of each of the syringes rests in a groove seat or the like. This prevents the syringe of the body from rotating along its axial length, as has been further illustrated in the foregoing cited U.S. Patent. The gang of syringes are held in their aligned seats by a movable hold down bar 16, which is provided with a releaseable lock.

The top surface of the illustrated TLC apparatus differs from that shown in the patent, previously cited, by the provision of an elongated anchoring rack 18 fixed to the top surface. Further details and operation of this anchoring rack will be described. The illustrated TLC apparatus shows means, such as a roll down bar 20, for gently lowering the gang of aligned needle tips, shown collectively as 22, towards the surface of the TLC plate 23. This leads to marked improvement in the discharge and lay down of the TLC sample on the TLC plate. The positive contact with the soft surface of the TLC plate prevents scoring of the plate surface.

Figure 2:
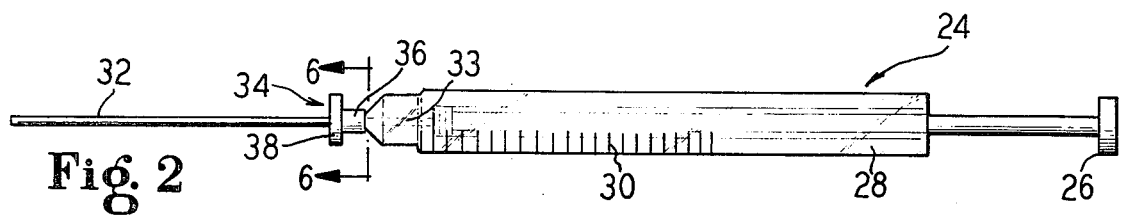
FIG. 2 is a side elevational view of a representative TLC discharge syringe illustrating a novel form of the anchoring element.

Looking now at FIG. 2, the new and improved TLC syringe is shown generally as 24, and such syringe has a conventional feature of a plunger 26; a glass syringe body or barrel 28, and volume gradations 30 along the length of the barrel. The discharge needle 32 is shown mounted to the forward end of the syringe barrel in communication with the passageway 33. The forward end refers to the direction of the path where the TLC syringe is conveyed for discharge.

Figure 6:
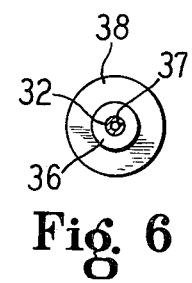
FIG. 6 is a cross sectional end view taken along line 6—6 of FIG. 2 of the anchoring element.

The anchoring element on the syringe 24 is shown as an integrally formed anchoring button 34. Such a button has a cylindrical stub 36 defining a circular passageway 37, see FIGS. 2 and 6. A flange plate 38 extends from one end of the cylindrical stub 36, and such flange plate does not reduce the diameter of the stub passageway 37. The flange plate is shown preferably in the form of a disc.

Figure 3:
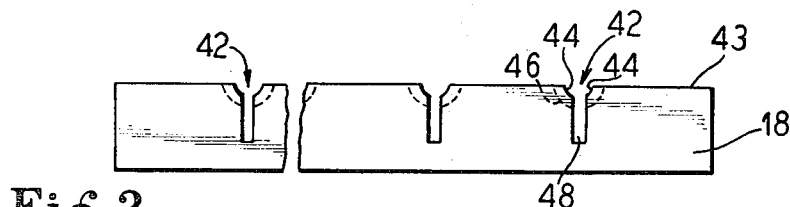
FIG. 3 is a front elevational view of the anchoring rack which is fixed to the top surface of the TLC apparatus to cooperate with the anchoring element illustrated in foregoing FIG. 2.
Figure 4:
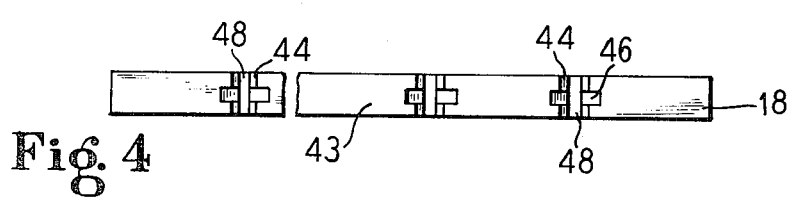
FIG. 4 is a top plan view of the elongated rack shown in the view of FIG. 3.

Reference will now be made to FIGS. 3 and 4 to understand in greater detail the elongated rack 18, previously illustrated at the top surface of the TLC apparatus. The anchoring rack has a plurality of anchoring seats 42 spaced along the top 43 of the elongated rack 18. Each anchoring seat is shown flanked by inclined sidewalls 44, and such inclined sidewalls merge with a transverse slot 46 which follows the long axis of the elongated rack 18. Such slot removably engages or seats the flange 38 of the anchoring element on the TLC syringe. Normal to the transverse slot 46 is a lowered needle slot or groove 48. The needle seated in groove 48 provides additional assurance against displacement. The transverse slot is preferably curvilinear where the flange is a disc plate.

Figure 5:
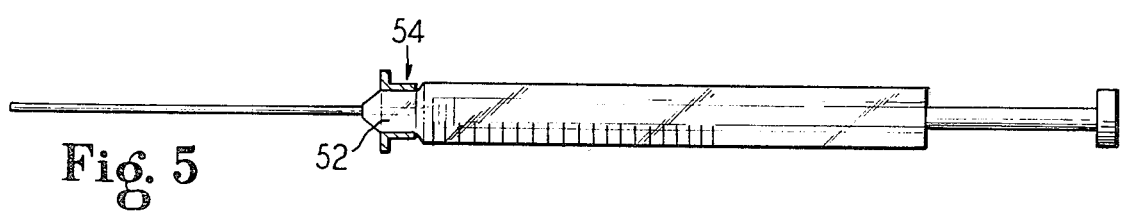
FIG. 5 is a side elevational view of another form of a TLC discharge syringe showing an alternative form of the anchoring element.

FIG. 5 illustrates an alternative form of mounting the anchoring element to a selected mounting area of the TLC syringe, such selective area indicated herein as the forward end of the syringe body 52. The anchoring button 52 is similar to anchoring button 34 described previously. The diameter of the cylindrical stub is, however, larger to accommodate the forward end of the syringe body 52. Such anchoring button is preferably bonded to the end of the syringe body. The form shown in FIG. 5 can similarly engage and disengage the anchoring seats in the anchoring rack with the flange plate seated in the transverse slot and the needle in the needle groove. The inclined walls may be concaval to better seat the syringe barrel.

In operation, engagement of the anchoring button with the anchoring rack secures the syringe against undesired axial and radial displacement. The axial, or forward and backward movement, of the syringe could result in the lowered needles scoring or damaging the TLC plate surface. In practice, the needles are gently lowered by means such as the roll down bar 20 to prevent such damage to the plate surface. The action of the pusher bar 10 against the plungers of the syringes exert such a forward force on the lowered needles. A backward movement could occur, for example, when the pusher bar action is stopped, and the pressure of the syringe bodies against the hold down bar is relieved. Other forces could result in backward movement.

It will be appreciated that increasing the pressure of the hold down bar 16 could prevent such undesired forward movement, if sufficiently great. The hazard of such a procedure is that the high pressures can result in breakage of the glass TLC syringe body. The improved anchoring means disclosed herein eliminates this hazard and allows slight hold down pressures to be operational.

The claims of the invention are now presented, and the terms of such claims may be further understood by reference to the terms in the preceding specification and in consideration of the views of the drawings.

What is claimed is:

1. An anchoring rack cradle and syringe assembly for use in conjunction with TLC apparatus comprising in combination,
   a syringe having a plunger, a cylindrical syringe body, volume gradations on said body, and a forward end for discharging TLC samples into a mounted needle,
   an anchoring button member fixed to a mounting area comprising a forward end of the syringe and the rearward end of the needle,
   said anchoring button member having a cylindrical stub defining a cylindrical path situated to be closely received and retained into a selected mounting area and a flange plate towards the forward end of the cylindrical stub,
   said flange plate being engageable with a fixed complimentary anchoring means on the TLC apparatus,
   said complimentary anchoring means on the TLC apparatus being formed by an anchoring rack cradle,
   said rack cradle including an elongated body positioned below said anchoring button member on said syringe,
   a plurality of transverse slots in said rack cradle to receive said flange plates of said syringe,
   each of said transverse slots in said rack cradle being aligned with said flange plate of said corresponding syringe,
   and inclined walls extending from the top of said rack cradle to each side of said transverse slot thereof to facilitate the positioning of said flange plate therein,
   whereby each of a gang of syringes may be aligned and positioned on the TLC apparatus thereby to prevent axial as well as radial movement of the syringes when positioned therein.

2. A syringe as in claim 1 wherein said flange plate is in the form of a disc.

3. A syringe as in claim 2 wherein the anchoring member is fixed to a selective area which is the forward end of the syringe body.

4. A syringe as in claim 3 wherein said cylindrical stub is retained to the forward end of the syringe by bonding means.

5. A syringe as in claim 4 wherein said cylindrical stub is retained to the forward end of the syringe body by means which increase frictional engagement.

6. A syringe as in claim 2 wherein the anchoring member is fixed to a selective area which is the rearward end of the needle.

7. A syringe as in claim 6 wherein said cylindrical stub is retained to the rearward end of the needle by a crimp interlocking the cylindrical stub to the barrel of the needle.

* * * * *